US010814015B2

(12) United States Patent
Dickey et al.

(10) Patent No.: US 10,814,015 B2
(45) Date of Patent: Oct. 27, 2020

(54) TRANSGENIC MOUSE MODEL FOR CONDITIONAL FKBP51 EXPRESSION AND RELATED METHODS (71) Applicant: University of South Florida, Tampa, FL (US)

(72) Inventors: Chad Dickey, Tampa, FL (US); Bo Zhang, Tampa, FL (US); Laura Jenelle Blair, Brandon, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/602,985

(22) Filed: May 23, 2017

(65) Prior Publication Data

US 2017/0258940 A1 Sep. 14, 2017

Related U.S. Application Data (63) Continuation of application No. 14/276,735, filed on May 13, 2014, now abandoned.

(51) Int. Cl.
| | |
|---|---|
| *A01K 67/00* | (2006.01) |
| *A01K 67/033* | (2006.01) |
| *A01K 67/027* | (2006.01) |
| *A61K 49/00* | (2006.01) |
| *C12N 9/90* | (2006.01) |
| *C12N 15/85* | (2006.01) |

(52) U.S. Cl.
CPC ...... *A61K 49/0006* (2013.01); *A01K 67/0278* (2013.01); *A61K 49/0008* (2013.01); *C12N 9/90* (2013.01); *C12N 15/8509* (2013.01); *A01K 2217/203* (2013.01); *A01K 2227/105* (2013.01); *A01K 2267/01* (2013.01); *A01K 2267/0356* (2013.01)

(58) Field of Classification Search
None
See application file for complete search history.

(56) References Cited

U.S. PATENT DOCUMENTS

| | | | |
|---|---|---|---|
| 4,736,866 A | | 4/1988 | Leder et al. |
| 5,942,435 A | * | 8/1999 | Wheeler ............ A01K 67/0271 435/325 |
| 6,004,941 A | | 12/1999 | Bujard et al. |
| 7,196,243 B2 | | 3/2007 | Gorczynski |
| 2014/0294798 A1 | | 10/2014 | Small et al. |

FOREIGN PATENT DOCUMENTS

WO    WO-2005/054500 A1    6/2005

OTHER PUBLICATIONS

Gallia et al ., 1998; Evaluation of an autoregulatory tetracycline regulated system Oncogene pp. 1879-1884.*
Miao et al., 2012; review Edited by Dr Patricia Hernandez-Rodriguez, pp. 255-282.*
Brevini et al., 2010, Theriogenology, vol. 74, pp. 544-550.*
Paris et al. (2010, Theriogenology, vol. 74, pp. 516-524.*
Munoz et al. (2008, Theriogenology, vol. 69, pp. 1159-1164.*
Petitte et al. (2004, Mech. of Develop., vol. 121, pp. 1159-1168.*
Lavial et al. (2010, Develop. Growth Diff., vol. 52, pp. 101-114.*
Tasic, Bosiljka etal., Site-specific integrase-mediated transgenesis in mice via pronuclear injection, PNAS Early Edition, approved Mar. 16, 2011, pp. 1-6, www.pnas.org/cgi/doi/10.1073/pnas.1019507108.
Chernajovsky, Yuti et at., Gene Therapy for Autoimmune Diseases: Quo Vadis?, Nature Reviews Immunology, Oct. 2004, 4(10):800-811, Nature Publishing Group.
O'Leary, John C. III et al., A New Anti-Depressive Strategy for the Elderly: Ablation of FKBP5/FKBP51, PloS one, Sep. 15, 2011, 6(9):e24840, https://doi.org/10.1371/journal.pone.0024840.
Gould, Thomas J. et al., Sensorimotor Gating Deficits in Transgenic Mice Expressing a Constitutively Active Form of $G_s\alpha$, Neuropsychopharmacology, Mar. 2004, 29(3):494-501, Nature Publishing Group.
Blair, Laura J. et al., Accelerated neurodegeneration through chaperone-mediated oligomerization of tau, The Journal of Clinical Investigation, Oct. 2013, 123(10):4158-4169.

(Continued)

Primary Examiner — Maria G Leavitt
(74) Attorney, Agent, or Firm — Meunier Carlin & Curfman LLC (57) ABSTRACT The subject invention pertains to transgenic non-human animals comprising a transgenic nucleotide sequence, integrated into the genome of the animals, comprising a nucleotide sequence encoding human FKBP51 operably linked to a tetracycline response element. In some embodiments, the transgenic animal comprises an additional transgenic nucleotide sequence, integrated into the genome of the animal, comprising a nucleotide sequence encoding a tetracycline transactivator (tTA) operably linked to a promoter; wherein the tTA is expressed upon activation of the promoter and binds the tetracycline response element, thereby causing expression of FKBP51. The invention also pertains to methods for screening for agents for the prevention and/or treatment of psychiatric disorders, such as depression.

4 Claims, 5 Drawing Sheets (56) References Cited

OTHER PUBLICATIONS

Sigmund, Curt D., Viewpoint: Are studies in Genetically Altered Mice Out of Control?, Arteriosclerosis, Thrombosis, and Vascular Biology, Jun. 2000, 20:1425-1429, American Heart Association, Dallas, Texas, downloaded from atvb.ahajournals.org on Feb. 8, 2008.
Moreadith, Randall Wade et al., Gene targeting in embryonic stem cells: the new physiology and metabolism, J Mol Med, Mar. 1997, 75(3):208-216, Springer-Verlag.
Keefer, C.L., Production of bioproducts through the use of transgenic animal models, Animal Reproduction Science, Jul. 2004, 82-83:5-12, Elsevier B.V.
Stechschulte, Lance A. et al., FKBP51 Reciprocally Regulates GRα and PPARγ Activation via the Akt-p38 Pathway, Mol Endocrinol, Aug. 2014, 28(8):1254-1264, Endocrine Society.
Sinars, C. et al., Structure of the large FK506-binding protein FKBP51, an Hsp90-binding protein and a component of steroid receptor complexes, PNAS, Feb. 4, 2003, 100(3):868-873.
Ellsworth, K. A. et al., FKBP5 genetic variation: association with selective serotonin reuptake inhibitor treatment outcomes in major depressive disorder, Pharmacogenetics and Genomics, Mar. 2013, 23(3):156-166, Wolters Kluwer Health/ Lipincott Williams & Wilkins.
Cao, Weihuan et al., FKBP immunophilins and Alzheimer's disease: chaperoned affair, Journal of Biosciences, Aug. 2011, 36(3):493-498, Indian Academy of Sciences.
Gama Sosa, Miguel A. et al., Animal transgenesis: an overview, Brain Struct Funct, Mar. 2010, 214(2-3):91-109, Springer-Verlag.
Bagle, T.R. et al., Transgenic Animals and their Application in Medicine, International Journal of Medical Research & Health Sciences, Dec. 25, 2012, 2(1):107-116.
Miao, Xiangyang et al., Recent Advances and Applications of Transgenic Animal Technology, Polymerase Chain Reaction, May 30, 2012, 255-282, InTec.
Tet-Off® and Tet-On® Gene Expression Systems User Manual, Cloneteck, Oct. 2012, pp. 1-47, Clontech Laboratories, Inc., Mountain View, California.
Cohen, Batya et al., MRI detection of transcriptional regulation of gene expression in transgenic mice, Nature Medicine, Apr. 2007, 13(4):498-503, Nature Publishing Group.
Kistner, Andreas et al., Doxycycline-mediated quantitative and tissue-specific control of gene expression in transgenic mice, Proceedings of the National Academy of Sciences of the United States of America, Oct. 1, 1996, 93(20):10933-10938.
Gossen, Manfred et al., Studying Gene Function in Eukaryotes by Conditional Gene Inactiyation, Annual Review of Genetics, 2002, 36:153-173.
Tong, Chang et al., Production of p53 gene knockout rats by homologous recombination in embryonic stem cells, Nature Letters, Sep. 9, 2010, 467(7312):211-215, Macmillan Publishers Limited.
Hendriksen, Coenraad et al., New Techniques for Producing Transgenic Animals—a Mixed Blessing from Both the Scientific and Animal Welfare Perspectives, ATLA, 2014, 42(2):93-94, Editorial.
Combes, R.D. et al., Every silver lining has a cloud: the scientific and animal welfare issues surrounding a new approach to the production of transgenic animals, ATLA, 2014, 42(2):137-145, Abstract.
Darcet, Flavie et al., Learning and memory impairments in a neuroendocrine mouse model of anxiety/depression, frontiers in Behavioral Neuroscience. May 1, 2014, 8(136):1-13, original Research Article.
Dubrovina, N.I. et al., Learning and Extinction of a Passive Avoidance Response in Mice with High Levels of Predisposition to Catalepsy, Neuroscience and Behavioral Physiology, Jun. 2009, 39(5):475-480, Springer Science+Business Medial, Inc.
Sanders Williams, R. et al, Transgenic animals in integrative biology: approaches and interpretations of outcome, Journal of Applied Physiology, Mar. 1, 2000, 88(3):1119-1126, American Physiological Society.

\* cited by examiner

ABSTRACT

TRANSGENIC MOUSE MODEL FOR CONDITIONAL FKBP51 EXPRESSION AND RELATED METHODS

CROSS-REFERENCE TO RELATED APPLICATIONS

This application is a continuation of U.S. application Ser. No. 14/276,735, filed May 13, 2014, now abandoned, the disclosure of which is incorporated herein by reference in its entirety.

GOVERNMENTAL SUPPORT

This invention was made with government support under Grant No. NS073899 awarded by National Institutes of Health. The government has certain rights in the invention.

BACKGROUND OF THE INVENTION

FKBP51, a protein that naturally increases with age in both mice and humans, is a heat shock protein 90 (Hsp90) co-chaperone as well as a glucocorticoid receptor (GR) regulator. Studies have linked polymorphisms in the FKBP51 gene with various psychiatric disorders, including PTSD, bipolar disorder, and major depression. The interaction between FKBP51 and the GR largely depends on levels of FKBP51 relative to GR. A previous study using FKBP51 knockout mice indicated that mice lacking FKBP51 were resistant to stress-induced depressive-like behavior.

BRIEF SUMMARY OF THE INVENTION

Aspects of the present invention provide a transgenic non-human animal comprising a transgenic nucleotide sequence, integrated into the genome of the animal, comprising a nucleotide sequence encoding human FKBP51 operably linked to a tetracycline response element. In some embodiments, the transgenic nucleotide sequence is inserted at a specific and/or non-disruptive chromosomal locus, such as for example, but not limited to, the Hip11 locus. In some embodiments, the transgenic animal comprises an additional transgenic nucleotide sequence, integrated into the genome of the animal, comprising a nucleotide sequence encoding a tetracycline transactivator (tTA) operably linked to a promoter; wherein the tTA is expressed upon activation of the promoter and binds the tetracycline response element, thereby causing expression of FKBP51. Furthermore, in certain embodiments, tTA is unable to bind the tetracycline response element in the presence of tetracycline, or a tetracycline derivative (such as, but not limited to, doxycycline, thereby inhibiting expression of the nucleotide sequence encoding human FKBP51 in the transgenic animal.

In one embodiment, the transgenic animal is a mouse.

In one embodiment, the promoter utilized in operable linkage with tTA is selected from the group consisting of a constitutive promoter, a tissue-specific promoter, a development-stage-specific promoter, and an inducible promoter. In some embodiments, the promoter is a tissue-specific promoter. The tissue-specific promoter may be a brain specific promoter, and in such embodiments, the tTA is expressed in the brain and binds the tetracycline response element, thereby causing expression of FKBP51 in the brain.

In one embodiment, a tissue-specific promoter utilized in operable linkage with tTA is a Ca2+/calmodulin-dependent protein kinase II (CaMKIIa) promoter that is specific for the forebrain, wherein tTA is expressed in the forebrain and binds the tetracycline response element, thereby causing expression of FKBP51 in the forebrain.

In some embodiments, the transgenic animals of the present invention exhibit depressive behavior.

In another aspect, the present invention provides methods for screening therapeutic agents for the treatment of one or more psychiatric disorder, comprising: (a) administering an agent to a transgenic animal of the present invention; (b) determining the effect of the agent on one or more phenotype of the one or more psychiatric disorder; and (c) comparing the effect to an untreated control animal, wherein an improvement in any one or more of the phenotypes indicates the agent is a therapeutic agent.

In one embodiment, the one or more psychiatric disorder is selected from the group consisting of post-traumatic stress disorder, bipolar disorder, depression and combinations thereof.

In another aspect, the present invention provides methods for screening therapeutic agents for the treatment of depressive-like behavior, comprising: (a) administering an agent to a transgenic animal of the present invention; (b) determining the effect of the agent on one or more phenotype of the depressive-like behavior; and (c) comparing the effect to an untreated control animal, wherein an improvement in any one or more of the phenotypes indicates the agent is a therapeutic agent.

In another aspect, the present invention provides methods for screening for an agent for the prevention or treatment of accumulation of FKBP51 in the forebrain, comprising: (a) providing a potential therapeutic agent; (b) administering the potential therapeutic agent to the transgenic animal of the present invention; (c) determining whether because of the administering of the potential therapeutic agent, accumulation of FKBP51 in the forebrain of the transgenic animal is prevented or slowed by comparison to a control animal not treated with the agent.

DETAILED DISCLOSURE OF THE INVENTION

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Prior to setting forth the invention in detail, it may be helpful to the understanding thereof to define several terms, and these are accordingly set forth in the next section, below. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting of the invention. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

Aspects of the present invention provide transgenic, non-human animals that are capable of expressing levels of FKBP51 that are at least equal to, or higher than, endogenous levels of FKBP51 in a tissue-specific and/or inducible manner.

This invention utilizes a system for regulating expression of eukaryotic genes using components of the Tet repressor/operator/inducer system of prokaryotes. In the system, transcription of a nucleotide sequence operably linked to at least one tet operator sequence is stimulated by a tetracycline (Tc)-controllable transcriptional activator fusion protein (referred to herein as tTA). In some embodiments, the tTA is comprised of two polypeptides. The first polypeptide is a Tet repressor (TetR; e.g., a Tn10-derived TetR), which binds to tet operator sequences in the absence but not the presence of Tc. The second polypeptide directly or indirectly activates transcription in eukaryotic cells. For example, the second polypeptide can be a transcriptional activation domain from herpes simplex virus virion protein 16 or another transcriptional activating domain, e.g. acidic, proline-rich, serine/threonine-rich, glutamine-rich. Alternatively, the second polypeptide can be a domain (e.g., a dimerization domain) which recruits a transcriptional activator (e.g., an endogenous transcriptional activator) to interact with the tTA fusion protein by a protein-protein interaction (e.g., a non-covalent interaction). In the absence of Tc or a Tc analogue, transcription of a gene operably linked to a tTA-responsive promoter (typically comprising at least one tet operator sequence and a minimal promoter) is stimulated by a tTA, whereas in the presence of Tc or a Tc analogue, transcription of the gene linked to the tTA-responsive promoter is not stimulated by the tTA.

Aspects of the invention also provide cells derived from transgenic animals of the present invention or cells transfected with expression constructs utilized in generation of the transgenic animals. Expression of the FKBP51 polynucleotide operably linked to a tTA-responsive promoter in a host cell of the invention can be inhibited by contacting the cell with tetracycline or a tetracycline analogue.

One aspect of the invention relates to non-human, transgenic animals having a transgene comprising a polynucleotide sequence encoding a tetracycline-controllable transactivator (tTA) and/or having a transgene encoding FKBP51 operably linked to a tTA-responsive promoter. Double transgenic animals having both transgenes (i.e., a tTA-coding transgene and FKBP51 linked to a tTA-responsive promoter) are also encompassed by the invention.

In some embodiments, the transgenic nucleotide sequence (s) is/are inserted at a specific and/or non-disruptive chromosomal locus, such as, but not limited to, the Hip11, ChAT, and ROSA26 loci. A site specific chromosomal locus can be targeted by the transgene utilizing site-specific integrase-mediated transgenesis previously described by Tasic et al. (2011). Briefly, a single-copy transgene is inserted into a predetermined chromosomal locus with high efficiency (up to about 40%). The method utilizes an integrase, such as phage ΦC31 integrase, to catalyze recombination between one or two attB sites in a recombinant DNA (transgene) with one or more tandem attP sites that are previously inserted into a specific locus in the animal's genome via standard homologous recombination-based methods in embryonic stem cells. In at least one embodiment, the FKBP51 transgene (a human FKBP51 cDNA encoding FKBP51) is flanked by attB sites and inserted at a specific locus containing one or more tandem attP sites. In another embodiment, the FKBP51 transgene (a human FKBP51 cDNA encoding FKBP51) is operably linked with tetracycline operon repeats, to conditionally drive expression of FKBP51 utilizing the Tet-Off system, and is flanked by attB sites and inserted at a specific locus containing one or more tandem attP sites. This allows for a single-copy transgene to be inserted into a predetermined chromosomal locus and also allows for conditional expression of the transgene via the Tet-Off system.

In one embodiment, the transgenic animal is a mouse. In other embodiments, the transgenic animal is a cow, a rat, a goat, a sheep or a pig.

Transgenic animals of the invention can be made, for example, by introducing a DNA molecule encoding tTA, or FKBP51 operably linked to a tTA responsive promoter, into a fertilized oocyte, implanting the fertilized oocyte in a pseudopregnant foster mother, and allowing the fertilized oocyte to develop into the non-human, transgenic animal to thereby produce the non-human, transgenic animal. Double transgenic animals can be created by appropriate mating of single transgenic animals to generate animals expressing tTA (driven by a promoter of choice) and FKBP51 operably linked to a tetracycline (tTA) responsive element (i.e., promoter) and a weak promoter, such as, but not limited to, the CMV minimal promoter element. Expression of FKBP51 operably linked to a tTA responsive promoter in a double transgenic animal of the invention can be inhibited by administering tetracycline or a tetracycline analogue to the animal.

Promoters useful in driving expression of tTA, thereby resulting in FKBP51 expression, include constitutive promoters, tissue-specific or development-stage-specific promoters, and inducible promoters. Constitutive promoters direct expression in virtually all tissues and are largely, if not entirely, independent of environmental and developmental factors. Tissue-specific or development-stage-specific promoters direct the expression of tTA in specific tissue(s) or at certain stages of development. Inducible promoters are not conditioned to endogenous factors but to environmental conditions and external stimuli that can be artificially controlled. Modulating factors can include, for example, light, oxygen levels, heat, cold and wounding. Since some of these factors are difficult to control outside an experimental setting, promoters that respond to chemical compounds, not found naturally in the organism of interest, are of particular interest. Along those lines, promoters that respond to antibiotics, metals, alcohols, steroids, among other compounds, are useful in the present invention to allow the induction of tTA activity, and subsequent FKBP51 expression following activation of the tTA responsive element, at will and independently of other biotic or abiotic factors.

In at least one embodiment, a tissue-specific promoter utilized in operable linkage with tTA is a Ca2+/calmodulin-dependent protein kinase II (CaMKIIa) promoter that is specific for the forebrain. By utilizing such a promoter, tTA is expressed in the forebrain and binds the tetracycline response element operably linked to the nucleotide encoding FKBP51, thereby causing expression of FKBP51 in a tissue specific manner in the forebrain. As a result, in some embodiments, the transgenic animals of the present invention exhibit depressive behavior.

In another aspect, the present invention provides methods for screening therapeutic agents for the treatment of one or more psychiatric disorder, comprising: (a) administering an agent to a transgenic animal of the present invention (which overexpresses FKBP51); (b) determining the effect of the agent on one or more phenotype of the one or more psychiatric disorder; and (c) comparing the effect to an untreated control animal, wherein an improvement in any one or more of the phenotypes indicates the agent is a therapeutic agent. In embodiments of the invention, the one or more psychiatric disorder is selected from the group consisting of post-traumatic stress disorder, bipolar disorder, depression and combinations thereof.

In another aspect, the present invention provides methods for screening therapeutic agents for the treatment of depressive-like behavior, comprising: (a) administering an agent to a transgenic animal of the present invention (which overexpresses FKBP51); (b) determining the effect of the agent on one or more phenotype of the depressive-like behavior; and (c) comparing the effect to an untreated control animal, wherein an improvement in any one or more of the phenotypes indicates the agent is a therapeutic agent.

In another aspect, the present invention provides methods for screening for an agent for the prevention or treatment of accumulation of FKBP51 in the forebrain, comprising: (a) providing a potential therapeutic agent; (b) administering the potential therapeutic agent to the transgenic animal of the present invention (which overexpresses FKBP51); (c) determining whether because of the administering of the potential therapeutic agent, accumulation of FKBP51 in the forebrain of the transgenic animal is prevented or slowed by comparison to a control animal not treated with the agent.

Agents/therapeutic agents can include, but are not limited to, chemical compounds, pharmaceutical compositions, biological compounds and compositions (e.g., proteins, DNA, RNA, siRNAs, vaccines and the like), and microorganisms.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Targeting Vector and Transgenic Mice

A transgenic mouse model was generated that conditionally over-expresses FKBP51 in discrete brain regions based on the Tet-Off expression system. For the FKBP51 transgenic model, a tet-regulatable construct was generated and validated and was targeted to a specific location in the genome for stable integration, preventing random insertional gene disruption. Gene insertion was verified via genotyping, and expression levels were verified using real-time PCR. The mice were crossed onto a CaMKIIa promoter-driven tet transactivator (tTA) to boost over-expression in the forebrain, where FKBP51 is predominantly found in normal mice. This model serves as a platform to test strategies aimed at depleting FKBP51.

The responder transgene was created by cloning a human FKBP51 cDNA into a tetracycline-inducible vector (Tet-Op-mp1pA); a pBluescript II SK phagemid containing bacteria derived tetracycline-responsive promoter element (TRE) consisting of the Tet operon (TetO), seven identical repeats of a 19 base-pair tet operator sequence, followed by a human derived minimum CMV (cytomegalovirus) promoter.

Figure 1:
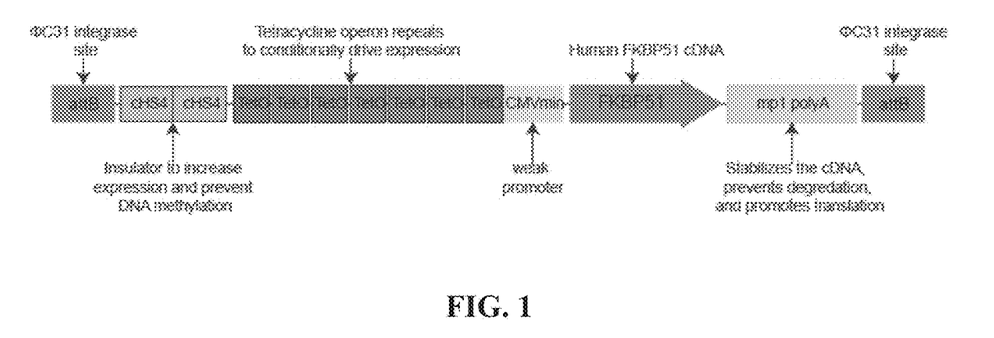
FIG. 1 shows a schematic of the targeting vector of embodiments of the present invention for transgenic production.

To prevent transcription interference with the transgene, a 2.4 kb fragment containing two copies of the chicken beta-globin insulator (cHS4) was subcloned upstream of the TetO sequences. This insulator has been shown to dramatically increase the expression of the subsequent cDNA sequence, and protects against DNA methylation. This TetO-FKBP51 transgene was then cut out using the added PmeI and existing NotI restriction sites and subcloned into a vector called pBT378 in between two bacteriophage derived attB sites that are recognized by the phage ΦC31 integrase. The process of integrase-mediated transgenesis in mice allows DNA to be inserted at a specific, non-disruptive chromosomal locus and is further described in Tasic et al, (2011), which is incorporated by reference in its entirety. These flanking attB sites allow for a high efficiency single-copy insertion of the gene into the attP-tagged permissive genomic site using ΦC31 integrase (see FIG. 1 for construct schematic). In the present example, the transgene was inserted at the Hipp11 locus on mouse chromosome 6.

Example 2

Evaluation of the Tet-Responsive FKBP51 Construct

Figure 2:
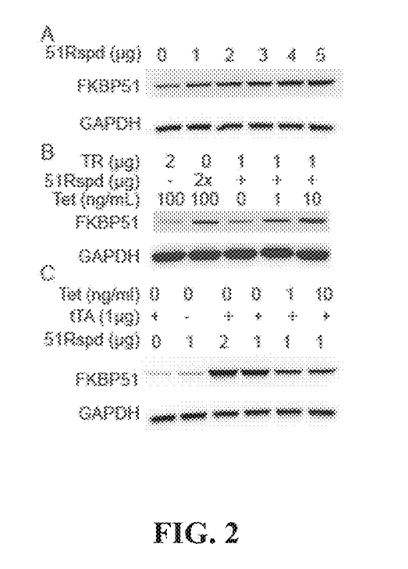
FIG. 2 shows the Tet-responsive FKBP51 construct of embodiments of the present invention behaves as expected in culture. HEK cells were transfected with indicated amounts of FKBP51 responder (51Rspd, A) and Tet-repressor (TR; B) or tet-transactivator (tTA; C) for 24 hours. Cells were then treated with indicated concentrations of tetracycline for 48 hours and lysates were analyzed by Western blot for FKBP51 and GAPDH.

The effectiveness and tet-responsiveness of the plasmid were evaluated in cells stably expressing the tet-repressor (FIG. 2). HEK cells were transfected with indicated amounts of FKBP51 responder (51Rspd; A), and Tet-repressor (TR; B) or tet-transactivator (tTA; C) for 24 hours. Cells were then treated with indicated concentrations of tetracycline for 48 hours and lysates were analyzed by Western blot for FKBP51 and GAPDH. The construct behaves as expected in culture, that is the FKBP51 responder (A) dose dependently increases the levels of FKBP51. The Tet-repressor (B) blocks expression of FKPB51, which then can be rescued dose dependently by tetracycline, mimicking what would happen when crossing a mouse made with this construct to rtTa mice. The tet-transactivator (C) drives FKBP51 expression, which can then be shut off by treatment with tetracycline, demonstrating what would happen when crossing a mouse with this vector with a tTa mouse.

Example 3

FKBP51 Expression in rTgFKBP5 Mice

Figure 3:
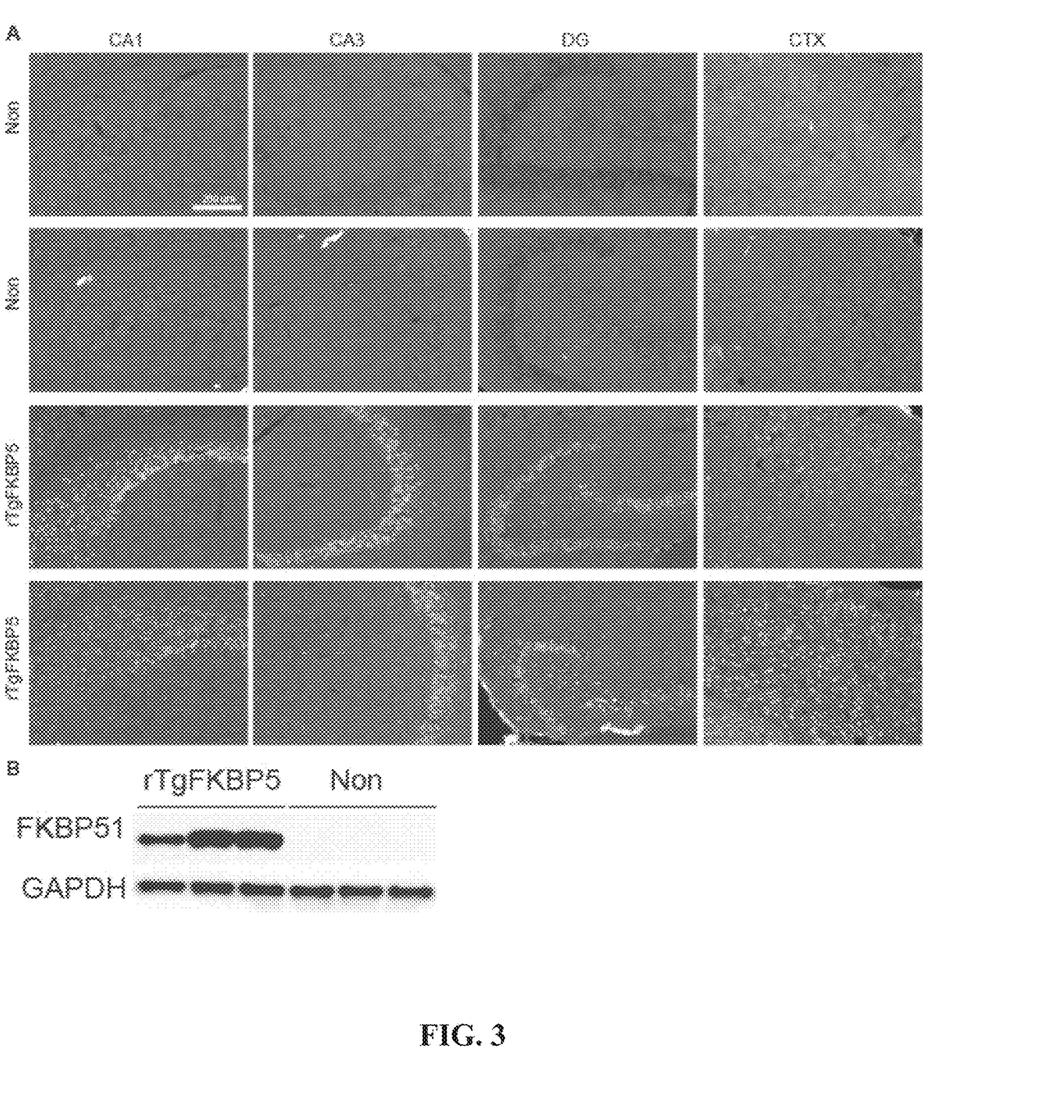
FIG. 3 shows FKBP51 levels in rTgFKBP5 mice. (A) Fluorescent staining of FKBP51 in the hippocampus (CA1, CA3, dentate gyms) and anterior cortex of non-transgenic and rTgFKBP5 mice. (B) Western blot analysis of FKBP51 levels in the anterior cortex of rTgFKBP5 and non-transgenic mice. Scale bar represents 200 μm. Mice utilized in the study are on a FVB/Swiss-Webster background.

Once crossed with tTA-CaMKIIa mice, FKBP51 overexpression was successfully detected by fluorescent staining (FIG. 3A) and Western blot (FIG. 3B). FKBP51 levels were higher in rTgFKBP5 mice vs. non-transgenic mice based on fluorescent staining of FKBP51 in the hippocampus (CA1, CA3, dentate gyms) and anterior cortex. Western blot analysis of FKBP51 levels in the anterior cortex of rTgFKBP51 and non-transgenic mice also revealed significantly higher levels of FKBP51 in the rTgFKBP5 mice.

Example 4

Phenotypes of the rTgFKBP5 Mice

Figure 4:
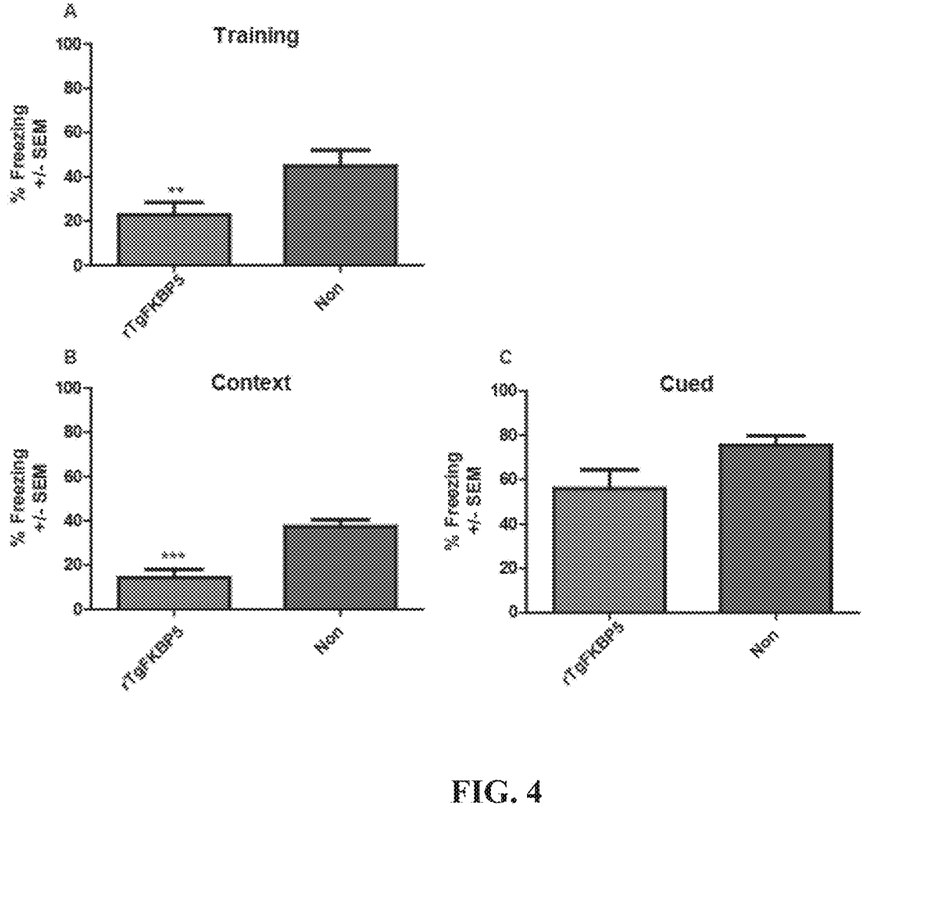
FIG. 4 shows rTgFKBP5 mice have a training deficit in fear conditioning. rTgFKBP5 and non-transgenic mice were assessed for freezing in a fear conditioning paradigm. (A) Percent freezing in fear conditioning training immediately following second tone/shock. p=0.0352. Percent freezing was also measured during testing to (B) context *p=0.0009 and (C) cued p=0.0661.

Several behavioral phenotypes were detected at 6 months of age due to the overexpression of FKBP51 in rTgFKBP5 mice. A significant deficit in learning in the training portion of fear conditioning was detected (FIG. 4), which was maintained during context training and almost significantly impaired in cued testing. This could be indicative of a hippocampal deficit, since this is involved in the learning of the task.

Figure 5:
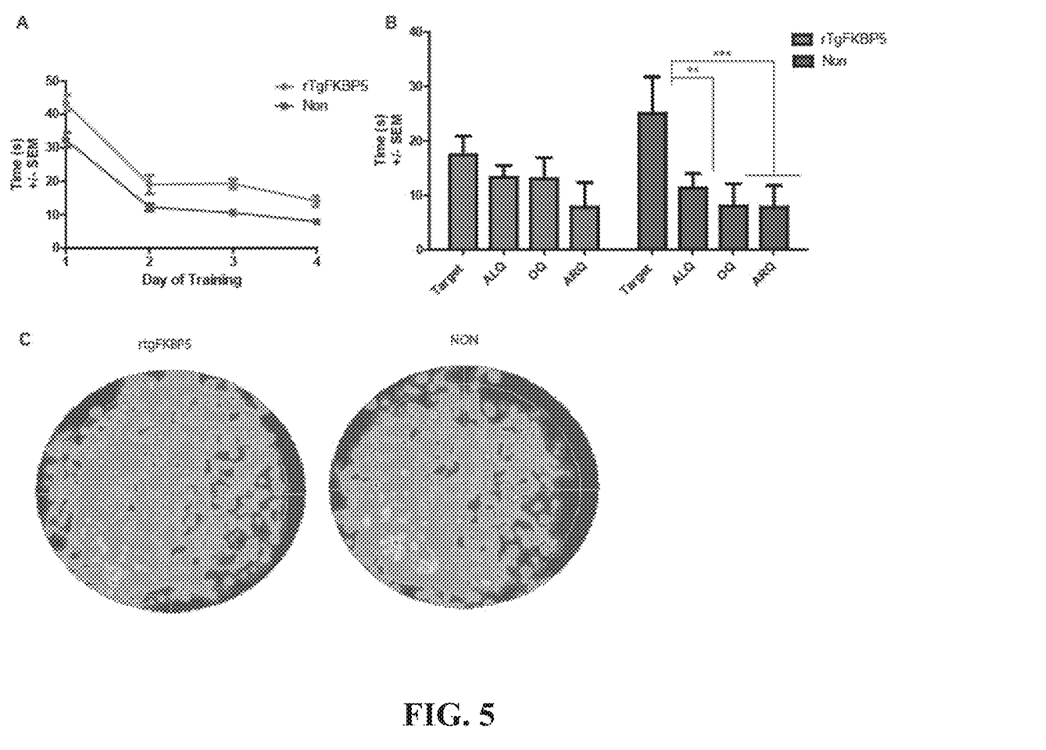
FIG. 5 shows rTgFKBP5 mice have a learning deficit in a Morris water maze. Six month old rTgFKBP5 and non transgenic mice were trained for four days to learn the location of the platform (A). On the fifth day, the platform was removed and mice were tested on their memory of the platform location using a one minute probe trial (B). p<0.01; *p<0.001. The heat map (C) of the combined mice in both groups is shown.

The Morris water maze behavioral task was performed on the same mice. There was a deficit (FIG. 5) in the probe trial of the rTgFKBP5 mice in remembering the location of the platform after four days of training. Additionally, these mice were also slower to learn the location of the platform in the training phase of the behavioral task.

Figure 6:
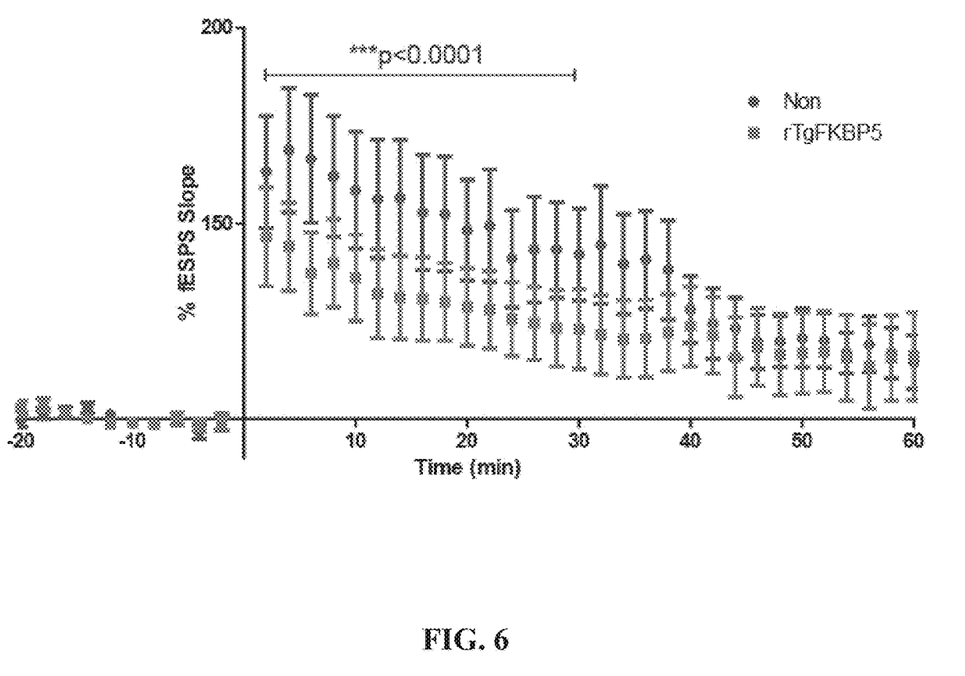
FIG. 6 shows eLTP deficits in rTgFKBP5 mice. Following a 20 minute baseline, 60 minutes LTP was measured following five 200 Hz Theta Burst stimulation.

At sacrifice, long term potentiation (LTP) electrophysiology was performed (FIG. 6), a cellular model of learning and memory on ex-vivo slices from 6 month rTgFKBP5 mice and non-transgenic controls. A deficit in early LIP was observed. eLTP deficiency has been shown previously to be a result of insufficient NMDA receptor activation.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Tasic, B., Hippenmeyer, S., Wang, C., Gamboa, M., Zong, H., Chen-Tsai, Y., and Luo, L. (2011) *Proc. Natl. Acad. Sci. USA* 108, 7902-7907.

We claim:
1. A method for screening for an agent for the prevention or treatment of accumulation of FKBP51 in the forebrain of a transgenic non-human mammal, comprising:
   providing a potential therapeutic agent;
   administering the potential therapeutic agent to a test transgenic non-human mammal, wherein the transgenic non-human mammal is chosen from a mouse, a rat, a goat, a sheep, and a pig;
   determining the level of FKBP51 in the forebrain of the test transgenic non-human mammal;
   identifying an agent as an agent for prevention or treatment of accumulation of FKBP51 in the forebrain when upon administering the potential therapeutic agent, the level of FKBP51 is reduced in the forebrain of the test transgenic non-human mammal compared to a control transgenic non-human mammal, wherein the control transgenic non-human mammal has the same genotype as that of the test transgenic non-human mammal and the potential therapeutic agent is not administered to the control transgenic non-human mammal;
   wherein each of the test and the control transgenic non-human mammals comprises integrated into its genome:
   i) a transgenic construct comprising a nucleotide sequence encoding a human FKBP51 operably linked to a tetracycline response element, and
   ii) a transgenic construct comprising a nucleotide sequence encoding a tetracycline transactivator (tTA) operably linked to a brain-specific promoter, wherein the tTA is expressed in cells of the forebrain of said test and the control transgenic non-human mammals,
   and wherein said tTA binds to the tetracycline response elements thereby causing expression in the forebrains of the test and the control transgenic non-human mammals of the human FKBP51.

2. The method according to claim 1, wherein the brain specific promoter is an inducible promoter.

3. The method according to claim 2, wherein the brain-specific promoter is a $Ca^{2+}$/calmodulin-dependent protein kinase II (CaMKIIa) promoter that is specific for the fore brain, wherein tTA is expressed in the forebrains and binds the tetracycline response elements, thereby causing expression of FKBP51 in the forebrains of the test and control non-human animals.

4. The method according to claim 3, wherein each of the test and control transgenic non-human animals is a mouse.

* * * * *